United States Patent [19]

Eckhardt et al.

[11] 4,287,210
[45] Sep. 1, 1981

[54] MICROBICIDAL META OXY- AND THIO-SUBSTITUTED PHENYLANILINES

[75] Inventors: Wolfgang Eckhardt, Lörrach, Fed. Rep. of Germany; Walter Kunz, Oberwil; Adolf Hubele, Magden, both of Switzerland

[73] Assignee: Ciba-Geigy Corporation, Ardsley, N.Y.

[21] Appl. No.: 97,026

[22] Filed: Nov. 21, 1979

[30] Foreign Application Priority Data

Nov. 27, 1978 [CH] Switzerland ............... 12118/78

[51] Int. Cl.³ .................. A01N 37/10; C07C 101/447
[52] U.S. Cl. .................................... 424/309; 560/9; 560/16; 560/21; 560/34; 560/43; 560/44; 548/262; 548/341; 548/342; 548/378; 548/336; 548/374; 549/60; 549/63; 260/456 A; 260/343.6; 260/347.2; 260/347.4; 260/501.11; 260/501.12; 260/438.1; 260/439 R; 424/269; 424/273 R; 424/273 P; 424/275; 424/276; 424/279; 424/285; 424/303

[58] Field of Search .................. 560/9, 16, 21, 44, 34, 560/43; 548/262, 341, 342, 378, 336, 374; 549/60, 63; 260/456 A, 343.6, 438.1, 439 R, 347.2, 347.4, 501.11, 501.12; 424/273 R, 273 P, 269, 275, 276, 279, 285, 303, 309

[56] References Cited

U.S. PATENT DOCUMENTS 4,093,738  6/1978  Hubele .................................. 560/43
4,151,299  4/1979  Hubele .................................. 560/43

OTHER PUBLICATIONS

Hubele, Chem. Absts., 84, 58964(t), 1976.
Hubele, Chem. Absts., 84, 30713(m), 1976.

Primary Examiner—G. T. Breitenstein
Attorney, Agent, or Firm—Frederick H. Rabin; Harry Falber

[57] ABSTRACT

There are described acylaniline derivatives which in the phenyl ring are substituted in the meta-position with respect to the amino group by an aliphatic oxymethyl group or aryloxymethyl group, or by an aliphatic thiomethyl group or arylthiomethyl group. Compounds of this type have a very favorable microbicidal spectrum. They are used principally for combating phytopathogenic fungi and bacteria.

8 Claims, No Drawings

MICROBICIDAL META OXY- AND THIO-SUBSTITUTED PHENYLANILINES

The present invention relates to a compound of the formula I, including salts and metal complexes thereof,

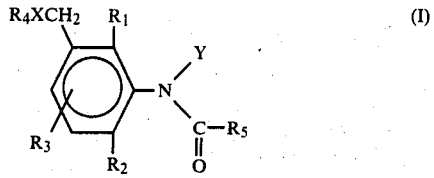

wherein
$R_1$ and $R_2$ independently of one another are each $C_1$–$C_4$-alkyl, $C_1$–$C_4$-alkoxy or halogen,
$R_3$ is hydrogen, halogen or methyl, the total number of carbon atoms in $R_1$, $R_2$ an $R_3$ not exceeding 6,
$R_4$ is $C_1$–$C_6$-alkyl which is unsubstituted or substituted by halogen, $C_1$–$C_4$-alkoxy or $C_1$–$C_4$-alkoxycarbonyl; or $R_4$ is $C_3$–$C_4$-alkenyl; $C_3$–$C_4$-alkynyl which is unsubstituted or substituted by halogen; or it is $C_3$–$C_7$-cycloalkyl; or phenyl which is unsubstituted or substituted by halogen, $C_1$–$C_3$-alkyl, $C_1$–$C_3$-alkoxy, nitro or trifluoromethyl; or $R_4$ is benzyl which is unsubstituted or substituted by halogen, $C_1$–$C_3$-alkyl or nitro,
X is oxygen or sulfur,
$R_5$ is 2-furyl or 2-tetrahydrofuryl each of which is unsubstituted or substituted by halogen; or $R_5$ is the group $CH_2Z$, where Z is one of the groups
(a) —$OR_6$,
(b) —$SR_6$,
(c) NH—$N(R_7)(R_8)$,
(d) —$OSO_2R_9$, or
(3) 1,2-pyrazole, 1,2,4-triazole or 1,3-imidazole, wherein
$R_6$ is $C_1$–$C_6$-alkyl, $C_3$–$C_4$-alkenyl or $C_3$–$C_4$-alkynyl,
$R_7$ is hydrogen or $C_1$–$C_3$-alkyl,
$R_8$ is $C_1$–$C_3$-alkyl, or phenyl which is unsubstituted or is substituted by halogen or methyl, and
$R_9$ is $C_1$–$C_4$-alkyl or mono- or di-($C_1$–$C_3$)-alkylamino, and
Y is

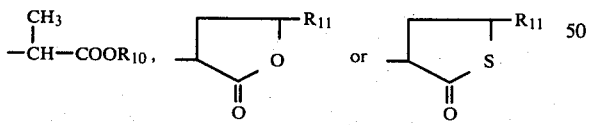

wherein
$R_{10}$ is $C_1$–$C_4$-alkyl which is unsubstituted or is substituted by halogen or $C_1$–$C_2$-alkoxy; or $R_{10}$ is $C_2$–$C_4$-alkenyl, $C_3$–$C_4$-alkynyl or $C_3$–$C_7$-cycloalkyl, and
$R_{11}$ is hydrogen or methyl.

By alkyl or by alkyl moiety of another substitute are meant, depending on the given number of carbon atoms, the following groups: methyl, ethyl, propyl, butyl, pentyl or hexyl, as well as isomers thereof, for example isopropyl, iso-butyl, sec-butyl, tert-butyl, iso-pentyl, and so forth.

Alkenyl is for example allyl, 2-butenyl, and so forth. Alkynyl is in particular propargyl. By $C_3$–$C_7$-cycloalkyl are meant cyclopropyl, cyclobutyl, cyclopentyl, cyclohexyl and cycloheptyl.

Halogen is fluorine, chlorine, bromine or iodine.

Examples of salt-forming acids are: inorganic acids such as hydrochloric acid, hydrobromic acid, hydriodic acid, sulfuric acid, phosphoric acid, phosphorus acid and nitric acid; and organic acids such as acetic acid, trichloroacetic acid, oxalic acid, succinic acid, maleic acid, lactic acid, glycolic acid, aconitric acid, citric acid, benzoic acid, benzenesulfonic acid and methanesulfonic acid.

Metal complexes of the compounds of the formula I consist of the basic organic molecule and an inorganic or organic melt salt, for example the halides, nitrates, sulfates, phosphates, tartrates, etc., of copper, manganese, iron and zinc and of other metals. The metal cations can be present here in the various valencies in which they occur.

The above lists containing the different examples constitute in no way any degree of limitation.

The invention relates in a narrower sense to compounds of the formula I wherein $R_1$ to $R_{11}$ and X have the meanings as defined, and Y is —$CH(CH_3)COOR_{10}$ or

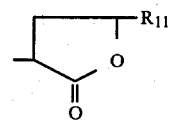

The compounds of the formula I can be produced by a whole series of methods, for example as follows. In the formulae II to IX, $R_1$ to $R_{11}$, X and Y have the meanings given under the formula I, "Hal" denotes halogen, preferably chlorine or bromine, and M is hydrogen or a metal cation, preferably an alkali metal cation or alkaline-earth metal cation.

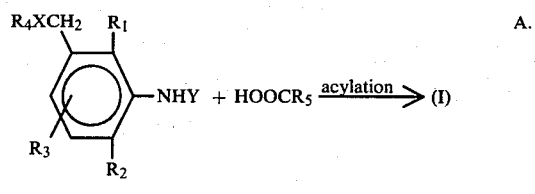

There is preferably used in this case a reactive derivative of a carboxylic acid of the formula III, for example the acid halide or the acid anhydride.

The use of acid-binding agents or condensation agents is in some cases advantageous. Examples of these are: tertiary amines such as trialkylamines (for example triethylamine), pyridine or pyridine bases such as 4-dimethylaminopyridine or 4-pyrrolidylopyridine, or inorganic bases, such as the oxides, hydroxides, hydrogen carbonates, carbonates or hydrides of alkali metals and alkaline-earth metals, as well as sodium acetate. It is moreover possible to use as an acid-binding agent the starting product II, which in that case is advantageously added in excess.

Where an acid halide is used, the production process A can be performed also without an acid-binding agent. In this case, the passing through of nitrogen to expel the formed hydrogen halide is an expedient measure.

B. When $R_5$ is —$CH_2OSO_2R_9$:

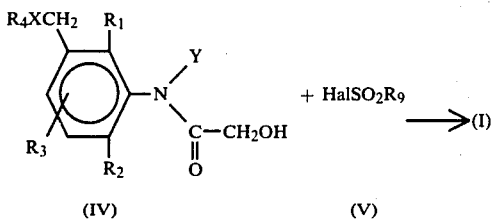

There is advantageously used a salt, particularly an alkali metal salt, of the compound of the formula IV. This process is performed if necessary in the presence of an acid-binding agent such as those described under A.

C. When $R_5$ is —$CH_2OR_6$, —$CH_2SR_6$, —$CH_2N$-H—$N(R_7)(R_8)$, 1,2-pyrazolylmethyl, 1,2,4-triazolylmethyl or 1,3-imidazolylmethyl:

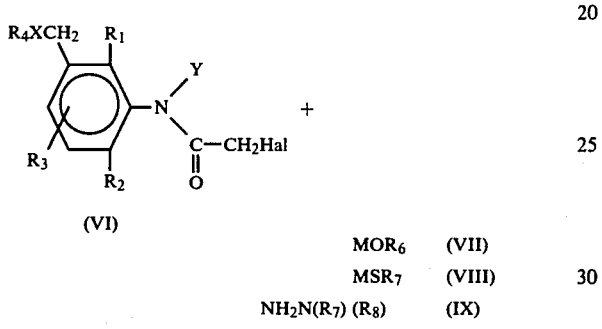

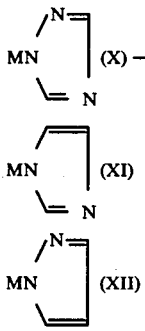

If M is hydrogen, the use of a salt-forming agent is appropriate, such as an oxide, hydroxide, hydride, etc., of alkali metals or alkaline-earth metals. With the use of starting materials of the formula IX, the final product is obtained as halide.

It is possible with mild bases to obtain therefrom at room temperature, or at slightly elevated temperature, the free hydrazino compound. Suitable for this are for example alkali carbonates.

Solvents which are inert to the reactants can be used in all processes. Examples of suitable solvents are: aliphatic hydrocarbons, such as benzene, toluene, xylenes and petroleum ether; halogenated hydrocarbons, such as chlorobenzene, methylene chloride, ethylene chloride and chloroform; ethers and ethereal compounds, such as dialkyl ether, dioxane and tetrahydrofuran; nitriles, such as acetonitrile; N,N-dialkylated amides, such as dimethylformamide; dimethylsulfoxide, ketones, such as methyl ethyl ketone; and mixtures of solvents of this type with one another.

The various processes likewise form part of the present invention.

All starting materials are produced by methods known per se; see in this respect:
J. Org. Chem. 30, 4101 (1965),
Tetrahedron 1967, 487,
Tetrahedron 1967, 493,
German Offenlegungsschrift No. 2,417,781,
German Offenlegungsschrift No. 2,311,897,
U.S. Pat. No. 3,780,090,
U.S. Pat. No. 3,598,859,
G.B. Patent Specification No. 1,438,311,
U.S. Pat. No. 3,933,860,
German Offenlegungsschrift No. 2,702,102, and
German Offenlegungsschrift No. 2,405,183.

A nitrobenzene substituted by $R_3$ and by $R_1$ and $R_2$ in the two ortho-positions is subjected to chloromethylation followed by reaction with a (thio)alcoholate $MXR_4$ (M is a metal cation, for example Na+). After catalytic hydrogenation of the nitro group, there is obtained the corresponding aniline derivative, from which there is obtained, by reaction with for example a halide Hal'-Y, the intermediate product of the formula II, from which are obtainable, by acylation, the intermediates of the formula IV or VI.

The compounds of the formula I each contain, in the position adjacent to the $COOR_{10}$ group and in the lactone group

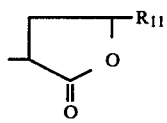

one asymmetrical carbon atom, and in the case where $R_{11}$ is $CH_3$ a further asymmetrical carbon atom, and can be split in the customary manner into optical isomers and diastereoisomers, respectively. The compounds of the formula I can be used on their own or together with suitable carriers and/or other additives. Suitable carriers and additives can be solid or liquid, and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

Solid Preparations:
Dusts and scattering agents (up to 10%); granulates [coated granules, impregnated granules and homogeneous granules] and pellets (1 to 80%);

Liquid Preparations:
(a) water-dispersible concentrates of active substance:
Wettable powders and pastes (25 to 90% in the commercial packing, 0.01 to 15% in ready-for-use solutions); emulsion concentrates and solution concentrates (10 to 50%; 0.01 to 15% in ready-for-use solutions);
(b) solutions (0.1 to 20%); and aerosols:
Compositions of the above types likewise form subject matter of the present invention.

It has now been found that compounds having the structure of the formula I surprisingly exhibit a very favourable microbicidal spectrum for practical requirements for the protection of cultivated plants. Cultivated plants within the scope of the present invention are for example: cereals, maize, rice, vegetables, sugar beet, soya bean, groundnuts, fruit trees or ornamental plants, especially however grape vines, hops, cucurbitaceae (cucumbers, pumpkins, melons), solanaceae, such as potatoes, tobacco and tomatoes, and also banana, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such microorganisms. The active substances are effective against the phytopathogenic fungi belonging to the following classes: Ascomycetes (for example Erysiphaceae or Venturia); Basidiomycetes, such as particularly rust fungi, Puccinia, Fungi imperfecti (for example Moniliales, Cercospora or Piricularia); and especially against the Oomycetes belonging to the Phycomycetes class, such as Phytophthora, Pythium or Plasmopara. Furthermore, they have an action against phytopathogenic bacteria, such as Xanthomonas sp., Pseudomonas sp., Erwinia as well as Corynebacterium. A strong bactericidal action against Xanthomonas sp. is exhibited in particular by the following compounds: Nos. 1.12, 1.15, 1.16, 1.26, 1.30 and 2.1 (0.06% concentration). The compounds of the formula I also have a systemic action. They can moreover be used as dressing agents for the treatment of seed (fruits, tubers, grain, etc.) and plant cuttings to protect them from fungus infections, and also against microorganisms occurring in the soil.

The present invention thus relates also to the use of the compounds of the formula I for combating phytopathogenic microorganisms.

The following subgroups are preferred:

Subgroup Ia $R_1$ is $CH_3$ or $OCH_3$,
$R_2$ is $CH_3$ or chlorine,
$R_3$ is hydrogen,
$R_4$ is $C_1-C_6$-alkyl,
X is oxygen,
Y is

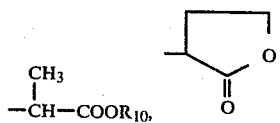 (= tetrahydrofuran-2-on-3-yl), wherein $R_{10}$ is $C_1-C_3$-alkyl,
$R_5$ is 2-furyl, 2-tetrahydrofuryl or $CH_2Z$, wherein Z is
(a) 1,2,4-triazol-1-yl,
(b) —$OR_6$ or —$SR_6$, wherein $R_6$ is $C_1-C_3$-alkyl, or

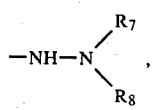

wherein $R_7$ and $R_8$ are each $C_1-C_3$-alkyl.

Subgroup Ib $R_1$ is $CH_3$ or $OCH_3$,
$R_2$ is $CH_3$,
$R_3$ is hydrogen,
$R_4$ is $C_1-C_6$-alkyl, X is oxygen,
Y is

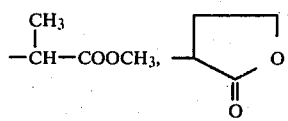

$R_5$ is 2-furyl, 2-tetrahydrofuryl or $CH_2$—Z, wherein Z is
(a) 1,2,4-triazol-1-yl,
(b) —$OR_6$, wherein $R_6$ is $C_1-C_3$-alkyl, or

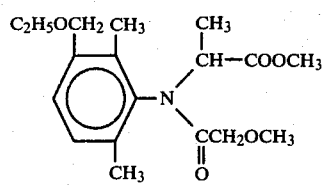

wherein $R_7$ and $R_8$ are $C_1-C_2$-alkyl.

Particularly preferred active substances of the subgroup Ia are those wherein $R_1$, $R_2$, $R_3$, X, Y and $R_{10}$ have the given meanings, whilst $R_4$ is sec-butyl, and $R_5$ is methoxymethyl.

Preferred individual compounds are the following compounds Nos. 1.7, 1.43, 1.45, 1.71, 1.76, 1.84 and 2.16.

The following Examples serve to further illustrate the invention without limiting its scope. Temperature values are given in degrees Centigrade, and percentages and parts relate to weight. Except where otherwise stated, the racemic mixture is meant in all cases where reference is made to an active substance of the formula I.

Production Examples

Example 1

Production of N-(1'-methoxycarbonyl-ethyl)-N-methoxyacetyl-2,6-dimethyl-3-ethoxymethyl-aniline of the formula

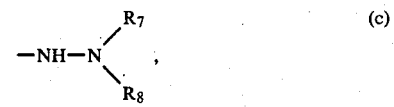

(a) 99 g of 2,6-dimethyl-3-ethoxymethylaniline, 167 g of 2-bromopropionic acid methyl ester and 67 g of sodium hydrogen carbonate were stirred for 20 hours at 140°; the mixture was then cooled, diluted with 400 ml of water, and extracted with diethyl ether. The extract was washed with a small amount of water, dried over sodium sulfate and filtered, and the ether was evaporated off. After the excess 2-bromopropionic acid methyl ester had been distilled off, the crude product was distilled under high vacuum; b.p. 123°/0.08 mbar.

(b) To 18.6 g of the ester obtained according to a) and 6.2 g of sodium carbonate in 80 ml of toluene, there was added dropwise with stirring, in the course of 5 minutes, 12.6 g of methoxyacetic acid chloride, the temperature rising during the addition from 20° to 50°. The reaction mixture was subsequently stirred for 60 minutes at room temperature; it was then filtered, and the solvent was evaporated off. The crude product was distilled under high vacuum; b.p. 160°–162°/0.08 mbar.

The following starting materials of the formula II can be produced in a manner analogous to that according to (a), or by one of the methods described herein:

| $R_1$ | $R_2$ | $R_3$ | $R_4X$ | Y | Physical data |
|---|---|---|---|---|---|
| $CH_3$ | $CH_3$ | H | $CH_3O$ | $-CH(CH_3)-COOCH_3$ | b.p. 105-107°/0.03mbar |
| $CH_3$ | $CH_3$ | H | $s.C_4H_9O$ | " | b.p. 155-160°/0.03mbar |
| $CH_3$ | $CH_3$ | H | $4\text{-}Cl-C_6H_4-S$ | " | b.p. 206-208°/0.09mbar |
| $CH_3$ | $CH_3$ | H | $CH_3OCCH_2S$ (O) | " | b.p. 172-174°/0.08mbar |
| $CH_3$ | $CH_3$ | H | $4\text{-}CH_3-C_6H_4O$ | (γ-butyrolactone ring) | m.p. 69-71° |
| $CH_3$ | $CH_3$ | H | $C_2H_5O$ | $-CH(CH_3)-COOCH_3$ | b.p. 123°/0.08mbar |
| $CH_3$ | $CH_3$ | H | $i\text{-}C_3H_7O$ | " | b.p. 112°/0.05mbar |
| $CH_3$ | $CH_3$ | H | $4\text{-}Cl-C_6H_4O$ | " | m.p. 74-76° |
| $CH_3$ | $CH_3$ | H | $2,4\text{-}Cl-C_6H_4O$ | " | m.p. 82,5-85° |
| $Ch_3$ | $CH_3$ | H | $C_6H_5CH_2O$ | " | b.p. 194-196°/0.08mbar |
| $CH_3$ | $CH_3$ | H | $nC_4H_9O$ | (γ-butyrolactone ring) | b.p. 190-192°/0.07mbar |

EXAMPLE 2

Production of N-(1'-methoxycarbonyl-ethyl)-chloroacetyl-2,6-dimethyl-3,2',4'-dichlorophenoxymethylaniline of the formula

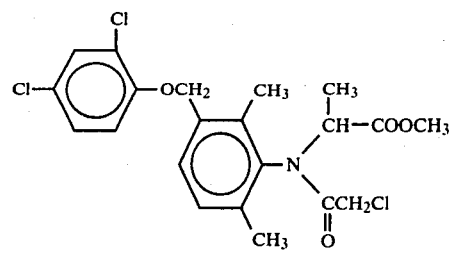

3.7 g of chloroacetyl chloride was added dropwise with stirring, within 10 minutes, to 11.5 g of N-(1'-methoxycarbonyl-ethyl)-2,6-dimethyl-3-2',4'-dichlorophenoxymethylaniline in 100 ml of toluene, in the course of which the temperature of the reaction mixture rose to 30°. The reaction mixture was then heated at 90° for 5 hours; the formed hydrogen chloride was removed by passing through nitrogen, and, after cooling, the solvent was evaporated off. The oily residue was distilled under high vacuum; b.p. 242°/0.07 mbar.

This compound can be reacted, according to process C, with compounds of the formulae VII to XII to corresponding compounds of the formula I.

The following compounds of the formula I can be produced in an analogous manner, or by one of the methods described herein:

TABLE I $(Y = -CH(CH_3)COOCH_3;\ R_1\ 2\text{-position})$

| Comp. No. | $R_1$ | $R_2$ | $R_3$ | $XR_4$ | $R_5$ | Physical constants |
|---|---|---|---|---|---|---|
| 1.1 | $CH_3$ | $CH_3$ | H | $CH_3O$ | $-CH_2OCH_3$ | b.p. 135-137°/0.11 mbar |
| 1.2 | $CH_3$ | $CH_3$ | H | $CH_3O(CH_2)_2O-$ | (tetrahydrofuranyl) | |
| 1.3 | $CH_3$ | $CH_3$ | 5-Cl | $n\text{-}C_3H_7O-$ | $-CH_2OCH_3$ | |
| 1.4 | $CH_3$ | $CH_3$ | H | $CH_3O(CH_2)_2O-$ | $-CH_2N$(triazolyl) | |
| 1.5 | $CH_3$ | $CH_3$ | 5-Cl | $i\text{-}C_3H_7O-$ | $-CH_2OCH_3$ | |
| 1.6 | $CH_3$ | $CH_3$ | 5-Cl | $n\text{-}C_3H_7O-$ | $-CH_2OC_2H_5$ | |
| 1.7 | $CH_3$ | $CH_3$ | 5-Cl | $s.C_4H_9O$ | $-CH_2OCH_3$ | b.p. 168°/0.03 mbar |
| 1.8 | $CH_3$ | $CH_3$ | H | $CH_3O-$ | $-CH_2OC_2H_5$ | b.p. 153-155°/0.04mbar |
| 1.9 | $CH_3$ | $CH_3$ | 5-Cl | $i\text{-}C_3H_7O-$ | $-CH_2OC_2H_5$ | |
| 1.10 | $CH_3$ | $CH_3$ | H | $CH_3O(CH_2)_2O-$ | (bromo-dioxane) | |
| 1.11 | $CH_3$ | $CH_3$ | 5-Cl | $s\text{-}C_4H_9O$ | $-CH_2OC_2H_5$ | |
| 1.12 | $CH_3$ | $CH_3$ | H | $CH_3O-$ | (dioxane) | b.p. 172-174°/0.11mbar |

TABLE I-continued (Y = —CHCOOCH$_3$; R$_1$ 2-position), with CH$_3$ on the CH

| Comp. No. | R$_1$ | R$_2$ | R$_3$ | XR$_4$ | R$_5$ | Physical constants |
|---|---|---|---|---|---|---|
| 1.13 | CH$_3$ | CH$_3$ | 5-Cl | i-C$_3$H$_7$O— | (tetrahydrofuranyl-O) | |
| 1.14 | CH$_3$ | CH$_3$ | H | CH$_3$O(CH$_2$)$_2$O— | (tetrahydrofuranyl-O) | |
| 1.15 | CH$_3$ | CH$_3$ | H | C$_2$H$_5$O— | —CH$_2$OCH$_3$ | b.p. 160–162°/0.08 mbar |
| 1.16 | CH$_3$ | CH$_3$ | H | (2,6-dichlorophenyl-O—) | —CH$_2$OC$_2$H$_5$ | oil |
| 1.17 | CH$_3$ | CH$_3$ | H | CH$_3$O(CH$_2$)$_2$O— | —CH$_2$OC$_3$H$_7$—i | |
| 1.18 | CH$_3$ | CH$_3$ | 4-Cl | C$_2$H$_5$O— | —CH$_2$OCH$_3$ | |
| 1.19 | CH$_3$ | CH$_3$ | H | C$_6$H$_5$—CH$_2$O | —CH$_2$OCH$_3$ | yellow oil |
| 1.20 | CH$_3$ | CH$_3$ | 5-Cl | i-C$_3$H$_7$O— | (tetrahydropyrrolyl N–H–O) | |
| 1.21 | CH$_3$ | CH$_3$ | H | CH$_3$O(CH$_2$)$_2$O— | —CH$_2$SCH$_3$ | |
| 1.22 | CH$_3$ | CH$_3$ | 4-Cl | C$_2$H$_5$O— | —CH$_2$OC$_2$H$_5$ | |
| 1.23 | CH$_3$ | CH$_3$ | 5-Cl | n-C$_4$H$_9$O— | —CH$_2$OCH$_3$ | |
| 1.24 | CH$_3$ | CH$_3$ | H | (4-chlorophenyl-O—) | (dihydrofuranyl-O) | yellow oil |
| 1.25 | CH$_3$ | CH$_3$ | 4-Cl | CH$_3$O— | —CH$_2$OCH$_3$ | |
| 1.26 | CH$_3$ | CH$_3$ | H | C$_2$H$_5$O— | —CH$_2$OC$_2$H$_5$ | b.p. 172–173°/0.08 mbar |
| 1.27 | CH$_3$ | CH$_3$ | H | CH$_3$O(CH$_2$)$_2$O | —CH$_2$OCH$_2$CH=CH$_2$ | |
| 1.28 | CH$_3$ | CH$_3$ | H | (4-chlorophenyl-O—) | —CH$_2$OC$_2$H$_5$ | b.p. 238°/0.11 mbar |
| 1.29 | CH$_3$ | CH$_3$ | H | CH$_3$O(CH$_2$)$_2$O— | —CH$_2$N(imidazolyl) | |
| 1.30 | CH$_3$ | CH$_3$ | H | C$_2$H$_5$O— | (dihydrofuranyl-O) | m.p. 119–123° |
| 1.31 | CH$_3$ | CH$_3$ | 4-Cl | CH$_3$O— | —CH$_2$OC$_2$H$_5$ | |
| 1.32 | CH$_3$ | CH$_3$ | H | s·C$_4$H$_9$O | —CH$_2$OC$_2$H$_5$ | b.p. 167–169°/0.07 mbar |
| 1.33 | CH$_3$ | CH$_3$ | 5-Cl | C$_2$H$_5$O— | —CH$_2$OCH$_3$ | |
| 1.34 | CH$_3$ | CH$_3$ | 5-CH$_3$ | C$_2$H$_5$O— | —CH$_2$OCH$_3$ | |
| 1.35 | CH$_3$ | CH$_3$ | H | (4-chlorophenyl-O—) | —CH$_2$OCH$_3$ | b.p. 237°/0.11 mbar |
| 1.36 | CH$_3$ | CH$_3$ | 5-Cl | n-C$_4$H$_9$O— | —CH$_2$OC$_2$H$_5$ | |
| 1.37 | CH$_3$ | CH$_3$ | H | CH$_3$O(CH$_2$)$_2$O— | —CH$_2$OCH$_2$C≡CH | |
| 1.38 | CH$_3$ | CH$_3$ | 5-Cl | C$_2$H$_5$O— | —CH$_2$OC$_2$H$_5$ | |
| 1.39 | CH$_3$ | CH$_3$ | H | CH$_3$O(CH$_2$)O— | CH$_2$NH—NH—C$_6$H$_5$ | |
| 1.40 | CH$_3$ | CH$_3$ | 5-CH$_3$ | C$_2$H$_5$O— | —CH$_2$OC$_2$H$_5$ | |
| 1.41 | CH$_3$ | CH$_3$ | 5-Cl | CH$_3$O— | —CH$_2$OC$_2$H$_5$ | |
| 1.42 | CH$_3$ | CH$_3$ | H | i-C$_3$H$_7$O— | (dihydrofuranyl-O) | b.p. 180–182°/0.08 mbar |
| 1.43 | CH$_3$ | CH$_3$ | 5-CH$_3$ | CH$_3$O— | —CH$_2$OCH$_3$ | b.p. 166°/0.07 mbar |
| 1.44 | CH$_3$ | CH$_3$ | H | CH$_3$O(CH$_2$)$_2$O— | —CH$_2$OCH$_3$ | |
| 1.45 | CH$_3$ | CH$_3$ | H | s·C$_4$H$_9$O— | —CH$_2$OCH$_3$ | b.p. 168–170°/0.07 mbar |
| 1.46 | CH$_3$ | CH$_3$ | 5-CH$_3$ | CH$_3$O— | —CH$_2$OC$_2$H$_5$ | |
| 1.47 | CH$_3$ | CH$_3$ | H | CH$_3$O(CH$_2$)$_2$O— | —CH$_2$OC$_2$H$_5$ | |
| 1.48 | CH$_3$ | CH$_3$ | H | C$_2$H$_5$O(CH$_2$)$_2$O— | —CH$_2$OCH$_3$ | |
| 1.49 | CH$_3$ | CH$_3$ | H | i-C$_3$H$_7$O— | —CH$_2$OCH$_3$ | b.p. 147–149°/0.11 mbar |

TABLE I-continued (Y = —CH(CH₃)COOCH₃; R₁ 2-position)

| Comp. No. | R₁ | R₂ | R₃ | XR₄ | R₅ | Physical constants |
|---|---|---|---|---|---|---|
| 1.50 | CH₃ | CH₃ | H | C₂H₅O(CH₂)₂O— | —CH₂OC₂H₅ | |
| 1.51 | CH₃ | CH₃ | H | i-C₃H₇S— | —CH₂OC₂H₅ | |
| 1.52 | CH₃ | CH₃ | H | O₂N—C₆H₄—O— | —CH₂OCH₃ | |
| 1.53 | Cl | Cl | H | CH₃O— | —CH₂OC₂H₅ | |
| 1.54 | CH₃ | CH₃ | H | i-C₃H₇O— | —CH₂OC₂H₅ | b.p. 164–166°/0.05mbar |
| 1.55 | CH₃ | CH₃ | H | CH₂=CH—CH₂— | —CH₂OCH₃ | |
| 1.56 | CH₃ | CH₃ | 5-Cl | CH₃O— | —CH₂OCH₃ | |
| 1.57 | CH₃ | CH₃ | H | CH₂=CH—CH₂O | —CH₂OC₂H₅ | |
| 1.58 | OCH₃ | Cl | H | CH₃O— | —CH₂OC₂H₅ | |
| 1.59 | CH₃ | CH₃ | H | CH₃O—C₆H₄—O | —CH₂OC₂H₅ | |
| 1.60 | CH₃ | CH₃ | H | C₆H₁₁—O— | —CH₂OC₂H₅ | |
| 1.61 | CH₃ | CH₃ | H | i-C₃H₇S— | —CH₂OCH₃ | |
| 1.62 | CH₃ | CH₃ | H | CH≡C—CH₂O— | —CH₂OCH₃ | |
| 1.63 | Cl | Cl | H | CH₃O— | —CH₂OCH₃ | |
| 1.64 | CH₃ | CH₃ | H | CH₃CH(COOC₂H₅)O— | —CH₂OCH₃ | |
| 1.65 | CH₃ | CH₃ | H | CH≡C—CH₂O— | —CH₂OC₂H₅ | |
| 1.66 | CH₃ | CH₃ | H | CH₃CH(COOC₂H₅)O— | —CH₂OC₂H₅ | |
| 1.67 | OCH₃ | CH₃ | H | C₂H₅O— | —CH₂OCH₃ | |
| 1.68 | CH₃ | CH₃ | H | C₆H₁₁—O— | —CH₂OCH₃ | |
| 1.69 | CH₃ | CH₃ | H | n-C₆H₁₃O— | —CH₂OCH₃ | |
| 1.70 | OCH₃ | Cl | H | C₂H₅O— | —CH₂OCH₃ | |
| 1.71 | CH₃ | CH₃ | H | C₆H₅CH₂O— | furyl | oil |
| 1.72 | CH₃ | CH₃ | H | s-C₄H₉O— | —CH₂N(triazolyl) | oil |
| 1.73 | CH₃ | CH₃ | H | n-C₆H₁₃O— | —CH₂OC₂H₅ | |
| 1.74 | CH₃ | CH₃ | H | CH₃OC(O)CH₂S— | —CH₂OCH₃ | b.p. 183–184°/0,06mbar |
| 1.75 | OCH₃ | CH₃ | H | CH₃O— | —CH₂OCH₃ | |
| 1.76 | CH₃ | CH₃ | H | s-C₄H₉O— | —CH₂NH—N(CH₃)₂ | oil |
| 1.77 | CH₃ | CH₃ | H | CH₃—C₆H₄—O— | —CH₂OCH₃ | |
| 1.78 | OCH₃ | CH₃ | H | CH₃O— | —CH₂OC₂H₅ | |
| 1.79 | CH₃ | CH₃ | H | s-C₄H₉O— | —CH₂OSO₂NHCH₃ | |
| 1.80 | CH₃ | CH₃ | H | s-C₄H₉O— | —CH₂OSO₂CH₃ | |
| 1.81 | CH₃ | CH₃ | H | C₆H₅CH₂O— | —CH₂OSO₂NHCH₃ | |
| 1.82 | CH₃ | CH₃ | H | C₆H₅CH₂O— | —CH₂OSO₂CH₃ | |
| 1.83 | CH₃ | CH₃ | H | s-C₄H₉O— | —CH₂OSO₂C₂H₅ | |
| 1.84 | CH₃ | CH₃ | 5-CH₃ | s-C₄H₉O— | —CH₂—O—CH₃ | b.p. 170°/0.06mbar |

TABLE II (Y = β-propiolactone ring; R₁ in 2-position)

| Comp. No. | R₁ | R₂ | R₃ | XR₄ | R₅ | Physical constants |
|---|---|---|---|---|---|---|
| 2.1 | CH₃ | CH₃ | H | n-C₄H₉O— | —CH₂OCH₃ | b.p. 206–209° |

TABLE II-continued (Y = [cyclopentanone with O]; R₁ in 2-position)

| Comp. No. | $R_1$ | $R_2$ | $R_3$ | $XR_4$ | $R_5$ | Physical constants |
|---|---|---|---|---|---|---|
| 2.2 | $CH_3$ | $CH_3$ | 5-Cl | $CH_3O-$ | $-CH_2OCH_3$ | /0.05 mbar |
| 2.3 | $CH_3$ | $CH_3$ | H | $CH_3O-$ | $-CH_2OCH_3$ | resin |
| 2.4 | $CH_3$ | $CH_3$ | 5-Cl | $CH_3O-$ | $-CH_2OC_2H_5$ | |
| 2.5 | $CH_3$ | $CH_3$ | H | $n-C_4H_9O-$ | $-CH_2OC_2H_5$ | b.p. 220–223°/0.07mbar |
| 2.6 | $CH_3$ | $CH_3$ | H | $CH_3O-$ | $-CH_2OC_2H_5$ | |
| 2.7 | $CH_3$ | $CH_3$ | H | $i-C_3H_7O-$ | $-CH_2OCH_3$ | |
| 2.8 | $CH_3$ | $CH_3$ | 5-Cl | $CH_3O-$ | [tetrahydrofuryl] | |
| 2.9 | $CH_3$ | $CH_3$ | 5-Cl | $C_2H_5O-$ | $-CH_2OC_2H_5$ | |
| 2.10 | $CH_3$ | $CH_3$ | H | $C_2H_5O$ | $-CH_2OCH_3$ | |
| 2.11 | $CH_3$ | $CH_3$ | H | $s.C_4H_9O-$ | $-CH_2OCH_3$ | resin |
| 2.12 | $CH_3$ | $CH_3$ | 5-Cl | $C_2H_5O-$ | $-CH_2OCH_3$ | resin |
| 2.13 | $CH_3$ | $CH_3$ | H | $C_2H_5O-$ | $-CH_2OC_2H_5$ | |
| 2.14 | $CH_3$ | $CH_3$ | H | $i-C_3H_7O-$ | $-CH_2OC_2H_5$ | |
| 2.15 | $CH_3$ | $CH_3$ | H | $s.C_4H_9O-$ | $-CH_2OSO_2NHCH_3$ | |
| 2.16 | $CH_3$ | $CH_3$ | 5-Cl | $s.C_4H_9O-$ | $-CH_2OCH_3$ | b.p. 222°/0,04 mbar |

TABLE III (Y = [cyclopentanone with S])

| Comp. No. | $R_1$ | $R_2$ | $R_3$ | $XR_4$ | $R_5$ | Physical constants |
|---|---|---|---|---|---|---|
| 3.1 | $CH_3$ | $CH_3$ | H | $CH_3O-$ | $-CH_2OC_2H_5$ | resin |
| 3.2 | $CH_3$ | $CH_3$ | H | $CH_3O-$ | $-CH_2OCH_3$ | resin |
| 3.3 | $CH_3$ | $CH_3$ | H | $CH_3O-$ | 2-tetrahydrofuryl | resin |
| 3.4 | $CH_3$ | $CH_3$ | H | $s.C_4H_9O-$ | $-CH_2OCH_3$ | resin |

Example 3

Granulate

The following substances are used to produce a 5% granulate:

5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution thus obtained is sprayed onto kaolin, and the acetone is subsequently evaporated off in vacuo. A microgranulate of this type is advantageously used for combating soil fungi.

Example 4

Wettable powder

The following constituents are used to produce (a) a 25% wettable powder and (b) a 10% wettable powder:

(a)

25 parts of active substance,
4.5 parts of calcium lignin sulfonate,
1.9 parts of Champagne chalk/hydroxyethyl cellulose mixture (1:1),
1.5 parts of sodium dibutyl naphthalene sulfonate,
19.5 parts of silicic acid,
19.5 parts of Champagne chalk, and
28.1 parts of kaolin;

(b)

10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in applicable mills and rollers. There are obtained wettable powders which have excellent wetting and suspension properties, and which can be diluted with water to give suspensions of the required concentration, and these are particularly suitable for leaf application.

Example 5

Emulsifiable concentrate

The following substances are used to produce a 25% emulsifiable concentrate:

25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the required concentration can be prepared from concentrates of this type by dilution with water, and these emulsions are especially suitable for leaf application.

BIOLOGICAL EXAMPLES

Example 6

Action against Phytophthora on tomato plants (a) Residual protective action

Tomato plants were sprayed, after 3-weeks' cultivation, with a spray liquor produced from wettable powder of the active substance (0.02% of active substance). After 24 hours, the treated plants were infested with a suspension of sporangia of the fungus. An assessment of the fungus infection was made after incubation of the infested plants during 5 days at 90–100% relative humidity of 20°.

(b) Residual curative action

After a cultivation period of three weeks, tomato plants were infested with a suspension of sporangia of the fungus. After an incubation time of 22 hours in a moist chamber at 20° C. with 90–100% relative humidity, the infested plants were dried, and subsequently sprayed with a spray liquor prepared from wettable powder of the active substance (0.02% of active substance). After drying of the applied coating, the treated plants were returned to the moist chamber. An assessment of fungus infection was made 5 days after infestation.

(c) Systemic action

A spray liquor prepared from wettable powder of the active substance (0.006% of active substance, relative to the volume of soil) was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants during 5 days at 20° with 90–100% relative humidity.

Compared with fungus infection occurring on the control plants (100% infection), the infection on plants treated with one of the following compounds was reduced to less than 10%: Nos. 1.1, 1.7, 1.8, 1.12, 1.15, 1.19, 1.24, 1.26, 1.28, 1.30, 1.32, 1.35, 1.42, 1.43, 1.45, 1.49, 1.54, 1.71, 1.76, 1.84, 2.1, 2.11 and 2.16.

Example 7

Action against Plasmopara viticola on grape vines

Grape-vine cuttings in the 4–5-leaf stage were sprayed with a spray liquor prepared from wettable powder of the active substance (0.02% of active substance). After 24 hours, the treated plants were infested with a suspension of sporangia of the fungus. The extent of fungus infection was assessed after incubation during 6 days at 20° with 95–100% relative humidity. Compared with the fungus infection present of the control plants (100% infection), the infection on plants which had been treated with one of the following compounds was reduced to less than 10%: Nos. 1.1, 1.7, 1.8, 1.12, 1.19, 1.26, 1.30, 1.32, 1.35, 1.42, 1.43, 1.45, 1.49, 1.54, 1.71, 1.76, 1.84, 2.1, 2.11 and 2.16.

Example 8

Action against Pythium debaryanum on sugar beet

Action after soil application

The fungus was cultivated on a carrot-chips nutrient solution, and applied to a soil/sand mixture. The soil infested in this manner was placed into flower pots, and sown with sugar-beet seeds. Immediately after sowing, the test preparations, formulated as wettable powders, were poured as aqueous suspensions over the soil (20 ppm of active substance, relative to the volume of soil). The pots were subsequently left for 2–3 weeks in a greenhouse at about 20° C. The soil was continuously maintained uniformly moist by light spraying.

Action after dressing application

The fungus was cultivated on a carrot-chips nutrient solution, and applied to a soil/sand mixture. The soil infested in this manner was placed into soil trays, and sown with sugar-beet seeds which had been dressed with the test preparations formulated as dressing powder (0.06% of active substance). The sown trays were left for 2–3 weeks in a greenhouse at about 20° C. The soil was maintained uniformly moist by light spraying.

In the evaluation of the test results, the sprouting of the sugar-beet plants and also the proportion of healthy plants and diseased plants were determined.

After treatment with the following compounds, over 80% of the sugar-beet seeds emerged, and the plants had a healthy appearance.

Compound Nos.: 1.1, 1.7, 1.8, 1.15, 1.19, 1.26, 1.30, 1.32, 1.43, 1.45, 1.49, 1.54, 1.74, 1.76, 1.84, 2.1, 2.11, 2.16 and 3.4.

Example 9

Action against Erysiphe graminis on barley

Residual protective action

Barley plants about 8 cm in height were sprayed with a spray liquor prepared from wettable powder of the active substance No. 1.74 (0.002% of active substance). After 3–4 hours, the treated plants were dusted with conidiospores of the fungus. The infested barley plants were kept in a greenhouse at about 22°, and the fungus infection was assessed after 10 days. The plants exhibited no signs of mildew.

What is claimed is:

1. A compound of the formula I, including salts and metal complexes thereof

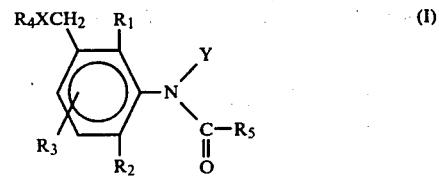

wherein $R_1$ and $R_2$ independently of one another are each $C_1$–$C_4$-alkyl, $C_1$–$C_4$-alkoxy or halogen, $R_3$ is hydrogen, halogen or methyl, the total number of carbon atoms in $R_1$, $R_2$ and $R_3$ not exceeding 6, $R_4$ is $C_1$–$C_6$-alkyl which is unsubstituted or substituted by halogen, $C_1$–$C_4$-alkoxy or $C_1$–$C_4$-alkoxycarbonyl; or $R_4$ is $C_3$–$C_4$-alkenyl; $C_3$–$C_4$-alkynyl which is unsubstituted or substituted by halogen; or it is $C_3$–$C_7$-cycloalkyl; or phenyl which is unsubstituted or substituted by halogen, $C_1$–$C_3$-alkyl, $C_1$–$C_3$-alkoxy, nitro or trifluoromethyl; or $R_4$ is benzyl which is unsubstituted or substituted by halogen, $C_1$–$C_3$-alkyl or nitro, X is oxygen or sulfur, $R_5$ is 2-furyl or 2-tetrahydrofuryl each of which is unsubstituted or substituted by halogen; or $R_5$ is the group $CH_2Z$, where Z is one of the groups
(a) —$OR_6$,
(b) —$SR_6$,
(c) NH—N($R_7$)($R_8$),
(d) —$OSO_2R_9$, or
(e) 1,2-pyrazole, 1,2,4-triazole or 1,3-imidazole,
wherein
$R_6$ is $C_1$-$C_6$-alkyl, $C_3$-$C_4$-alkenyl or $C_3$-$C_4$-alkynyl,
$R_7$ is hydrogen or $C_1$-$C_3$-alkyl,
$R_8$ is $C_1$-$C_3$alkyl, or phenyl which is unsubstituted or is substituted by halogen or methyl, and
$R_9$ is $C_1$-$C_4$-alkyl or mono- or di-($C_1$-$C_3$)-alkylamino, and
Y is

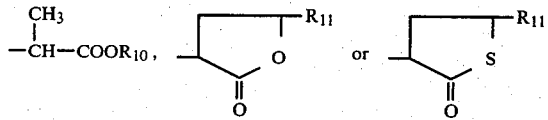

wherein
$R_{10}$ is $C_1$-$C_4$-alkyl which is unsubstituted or is substituted by halogen or $C_1$-$C_2$-alkoxy; or $R_{10}$ is $C_2$-$C_4$-alkenyl, $C_3$-$C_4$-alkynyl or $C_3$-$C_7$-cycloalkyl, and
$R_{11}$ is hydrogen or methyl.

2. A compound according to claim 1, wherein Y is —CH($CH_3$)$COOR_{10}$ or

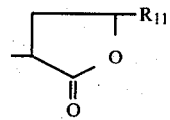

3. A compound according to claim 1, wherein $R_1$ is $CH_3$ or —$OCH_3$; $R_2$ is $CH_3$ or chlorine; $R_3$ is hydrogen; $R_4$ is $C_1$-$C_6$-alkyl; X is oxygen; Y is —CH($CH_3$)—$COOR_{10}$ or tetrahydrofuran-2-on-3-yl; $R_{10}$ is $C_1$-$C_3$-alkyl; $R_5$ is 2-furyl, 2-tetrahydrofuryl or —$CH_2Z$, where Z is 1,2,4-triazol-1-yl, —$OR_6$ or —$SR_6$ or —NH—N($R_1$)($R_8$), $R_6$, $R_7$ and $R_8$ independently of one another each being $C_1$-$C_3$-alkyl.

4. A compound according to claim 3, wherein $R_4$ is sec-butyl, and $R_5$ is methoxymethyl.

5. N-(1'-Methoxycarbonyl-ethyl)-N-methoxyacetyl-2,6-dimethyl-3-sec-butoxymethyl-aniline according to claim 4.

6. An insecticidal or fungicidal composition comprising (1) a bactericidally or fungicidally effective amount of compound according to claims 1, 2, 3, 4 or 5, and (2) an inert carrier.

7. A method for controlling or preventing an infection of phytopathogenic bacteria or fungi which comprises applying to plants a bactericidally or fungicidally effective amount of a compound according to claims 1, 2, 3, 4 or 5.

8. A method according to claim 7, wherein phytopathogenic fungi are controlled.

* * * * *